United States Patent [19]

Lahodny et al.

[11] Patent Number: 4,600,007
[45] Date of Patent: Jul. 15, 1986

[54] PARAMETRIUM CUTTING FORCEPS

[75] Inventors: Johann Lahodny, Gmünd, Austria; Ernst Dreier, Steckborn, Switzerland

[73] Assignee: Fritz Gegauf AG Bernina-Nähmaschinenfab., Steckborn, Switzerland

[21] Appl. No.: 640,309

[22] Filed: Aug. 13, 1984

[30] Foreign Application Priority Data

Sep. 13, 1983 [CH] Switzerland .................. 4972/83
Feb. 2, 1984 [EP] European Pat. Off. ...... 84810060.8

[51] Int. Cl.⁴ ............................................. A61B 17/32
[52] U.S. Cl. .................... 128/318; 128/321; 128/305; 30/131
[58] Field of Search ............. 128/318, 305, 321, 322, 128/323, 324; 30/131, 132, 254

[56] References Cited

U.S. PATENT DOCUMENTS 1,918,700  7/1983  Harris ................... 128/305
3,175,556  3/1965  Wood et al. ........... 128/305
4,452,246  6/1984  Bader et al. ........... 128/321

FOREIGN PATENT DOCUMENTS

WO83/00994  3/1983  PCT Int'l Appl.
GM8005113   5/1980  United Kingdom.

Primary Examiner—Robert Peshock
Assistant Examiner—John G. Weiss
Attorney, Agent, or Firm—Marmorek, Guttman & Rubenstein

[57] ABSTRACT

The forceps comprises clamping jaws which may be actuated clampwise by means of grips. One side edge of a first clamping jaw is in form of a cutting edge. On the side of the other clamping jaw lies a cutting blade which may cooperate with the cutting edge of the first clamping jaw for cutting the tissue clamped between the clamping jaws. The rest position of the cutting blade is determined by a catching device. The cutting blade engages below a protecting ramp in this catching device when the forceps is open. The forceps permits an easy, rational and proper working whereby injuries by uncontrollable and inadvertent motion of the cutting blade are excluded.

8 Claims, 4 Drawing Figures

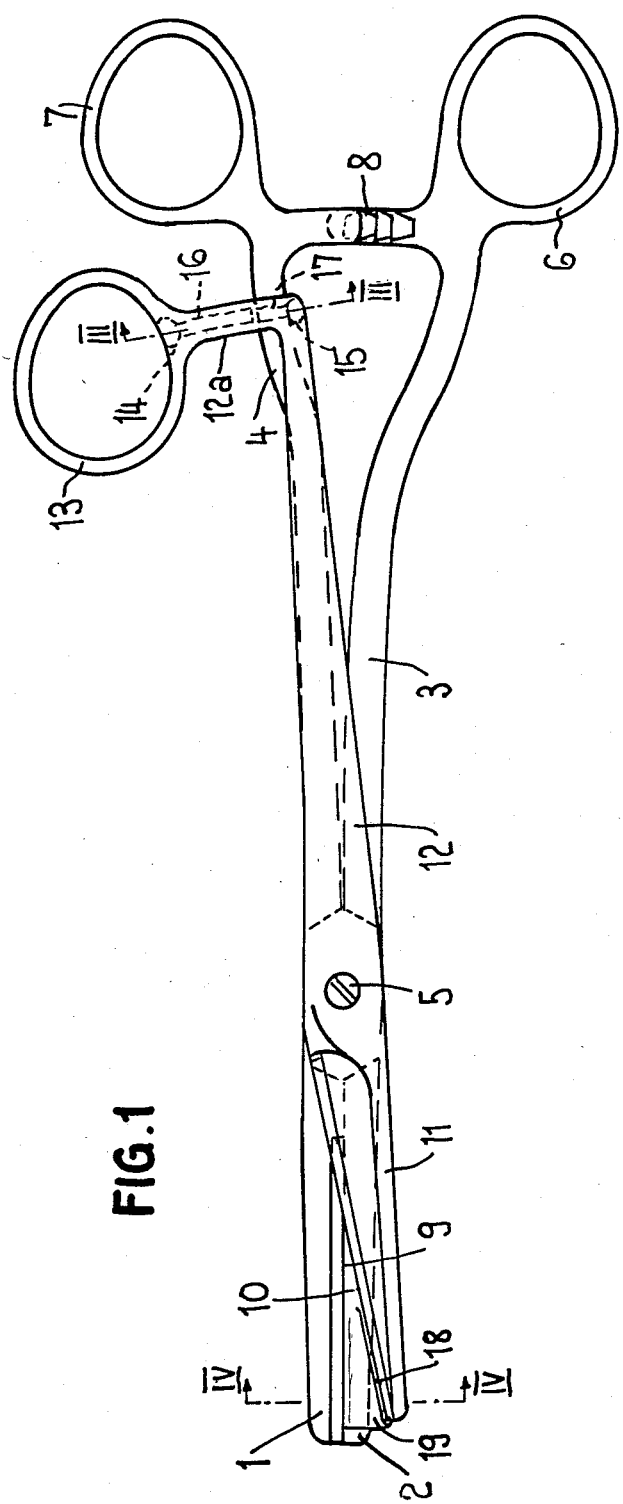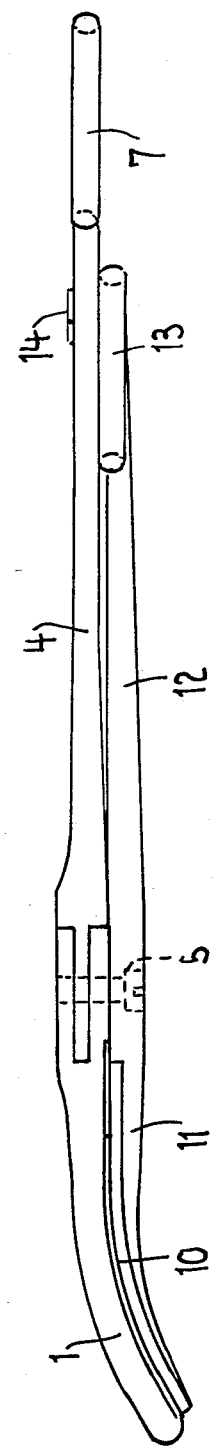
FIG.1
FIG.2

PARAMETRIUM CUTTING FORCEPS

BACKGROUND OF THE INVENTION

The present invention relates to a parametrium cutting forceps with clamping jaws, a locking device for stopping the clamping jaws in the clamping position and with a cutting blade. Known parametrium forceps serve for clamping of the tissue, more particularly of the parametrium between uterus and the pelvic wall at the time of a surgical removal of the uterus (DE-GM No. 80 05 113). Such known parametrium forceps serve exclusively one purpose, namely the clamping of tissue. Another additional instrument is necessary for the cutting procedure which not only renders more difficult and more prolonged the surgical procedure but bears also in itself the danger that tissue external to the clamped portion may become cut.

A dissector-obstructor apparatus is known from U.S. Pat. No. 3,175,556 which permits to clamp the vessels and then to cut them. This forceps permits by means of clamping jaws, to clasp a pair of clamps upon the vessels to be cut and closed and then to dissect or sever the vessels between the two clamps by means of a separately actuated cutting blade. However, the utilization of this known apparatus is limited to the closing and separation of vessels. Neither the apparatus nor the clamps to be clasped are capable to clamp the tissue in a continuous proceudre and then to cut it along the clamped portion.

A further forceps with clamping jaws is known for seizing a surgical needle and for cutting the sewing thread by means of a separately actuated cutting blade (PCT-Application WO83/00994). Also this forceps is not appropriate and not provided either for clamping the tissue nor for cutting the same along the side of the clamping jaws.

A surgical forceps is further known the jaws of which comprising longitudinal slits through which a cutting blade may pass for cutting the clamped tissue (U.S. Pat. No. 1 918 700). The cutting blade must be mounted to an arm of a double armed lever, this arm lying entirely at the outside of one of the jaws so that it must enclose an important angle with respect to the jaws when the cutting blade is ineffective and it lies consequently far away on the side which is disturbing and renders more difficult the introduction of the forceps in narrow cavities of the body. The cutting effect of a cutting blade which passes with play through slits of clamping jaws is not satisfactory.

SUMMARY OF THE INVENTION

The object of the present invention is to realize a parametrium cutting forceps which not only permits through the combination of clamping and cutting to considerably simplify and accelerate the operaion procedure but also guarantees a safe working by good accessibility in narrow cavities of the body. This problem is solved in that a mobile cutting blade is provided on the side of the clamping jaws, said cutting blade being movable from an ineffective open position adjacent to the side of one clamping jaw to the region of a counter cutting edge at one side of the other clamping jaw for cutting clamped tissue of a section of the length of the clamping jaws at the side of said clamping jaws. An additional increase of the safety and at the same time a simplification of the working may be achieved when the cutting edge of the cutting blade engages behind a protecting ramp of one clamping jaw in the open position of the jaws and of the cutting blade. This permits to avoid an injury of the tissue to be seized or of the neighbouring tissue by the open cutting blade when the open forceps is introduced for seizing and clamping of a section of the tissue. The cutting blade in its open, ineffective position, is preferably held behind the protecting ramp by a stopping or catching device. This ensures that the cutting blade cannot be accidentally swung out of its protected resting position before the cutting procedure is intentionally released. In this case, it is possible to dimension the catching force so that after the release of the catching device the clamped tissue is cut suddenly.

The parametrium cutting forceps according to the invention will be described further by way of example and with reference to the accompanying drawings.

BRIEF DESCRIPTION OF THE DRAWINGS

FIG. 1 is a lateral view of the parametrium cutting device,

FIG. 2 is a top view of the parametrium cutting device,

DESCRIPTION OF THE PREFERRED EMBODIMENT

Figure 4:
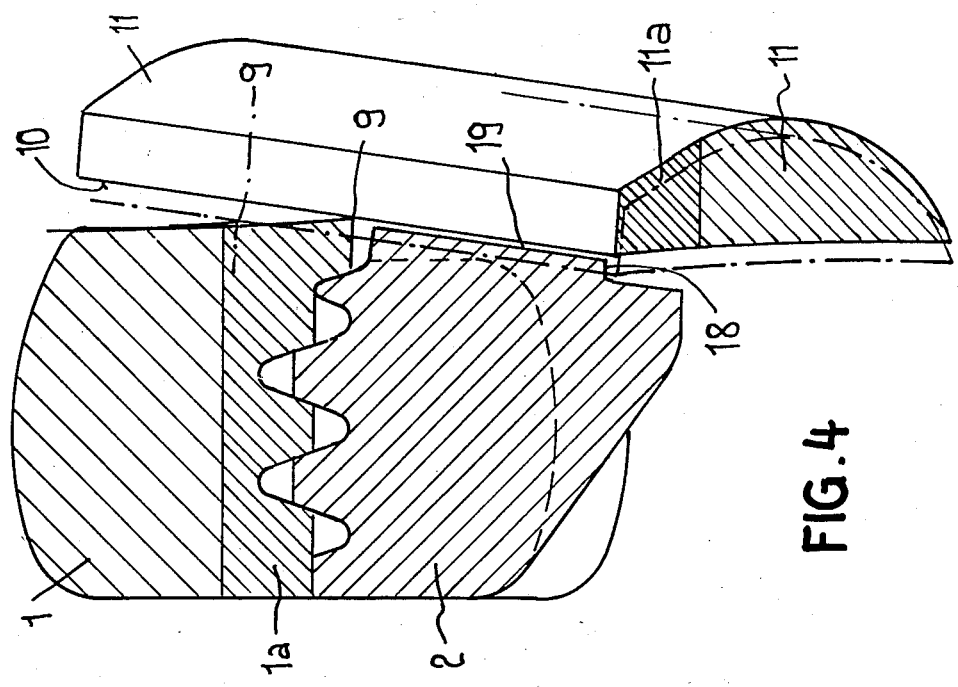
FIG. 4 is an enlarged section along the line IV—IV of FIG. 1.
Figure 3:
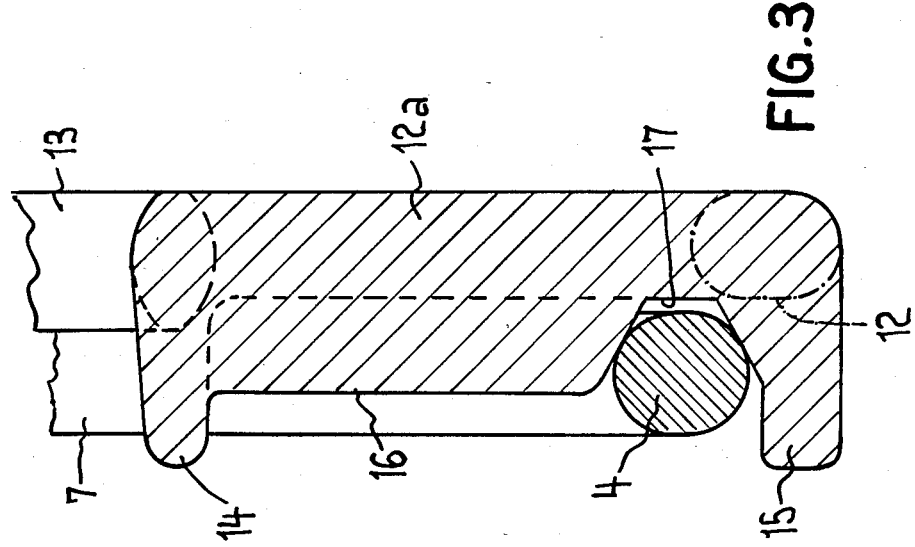
FIG. 3 is an enlarged section along the line III—III of FIG. 1.

The illustrated parametrium cutting forceps comprises an upper jaw 1 and a lower jaw 2 which are attached to branches 3 and 4, respectively, which are pivoted on a hinge screw 5. The branches 3 and 4 are provided with ring grips 6, and 7, respectively, which serve for the handling in a known way. Transverse arms of the branches 3 and 4 are provided with locking indentations 8 which permit to lock the forceps in different closed clamping positions. As indicated more particularly in FIG. 4 the upper clamping jaw 1 is faced with a clamping plate 1a of hard metal. This clamping plate as well as the upper side of the clamping jaw 2 are provided with longitudinal and transverse grooves which in their totality form a real indentation which considerably increases the adherence of the forceps to a tissue clasped between the clamping jaws. One side edge of the clamping plate 1a forms a cutting edge 9 along one side of the clamping jaw 1. It is provided for cooperation with a cutting edge 10 of a hard metal cutter 11a mounted on a cutting blade 11. The cutting blade 11 consists of a piece with a branch 12 the rear part 12a of which is bent toward the outside and completed with a ring grip 13. The cutting blade 11 is also pivoted on the screw 5. The rear end looking toward the outside of the branch 12 is in form of a catch projecting part which cooperates with the branch 4 of the lower clamping jaw 2 as a catching device. The catch projecting part comprises a flat part 16 between end stops 14 and 15 and at the internal part a catching recess 17. The branch 4 lies in the catching recess 17 when the cutting blade 11 is in the ineffective catch position illustrated in FIGS. 1 and 3. In this catch position, the cutting blade in accordance with FIG. 4 lies somewhat below a shoulder 18 at the lower side of a protecting ramp 19 of the lower clamping jaw 2. As indicated in FIG. 1, the shoulder 18, respectively the lower limiting surface of the protecting ramp 19 is inclined according to the inclination of the cutting edge 10 of the cutting blade 11 so that this cutting edge 10 lies in a regular distance somewhat under the shoulder 18 in the illustrated catch position of the cutting blade. In this way, the cutting edge 10 of the cutting blade 11 may engage under the shoulder 18 as indicated by the dot-and-dash line in FIG. 4. As indicated in FIG. 1, the shoulder 18 projects somewhat in front over the cutting edge 10 so that in the engaged position indicated by the dot-and-dash line, the cutting edge lies under the protecting ramp 19 and it is entirely protected and ineffective. In the closed position of the forceps illustrated in the Figures for which the locking indentations 8 are engaged, the relatively far below lying cutting edge 9 of the clamping plate 1a of the upper clamping jaw pushes the cutting blade 11 in the outer position indicated in continuous line in which its cutting edge 10 lies somewhat outside of the protecting ramp 19. If the forceps is still stronger squeezed, the cutting blade 11 is still pushed somewhat toward the outside. When the forceps is open, the cutting edge 9 of the upper clamping jaw lies further above as indicated in FIG. 4 by the dot-and-dash line and it liberates the cutting blade 11 so far that its cutting edge 10 may enter below the shoulder 18.

For working with the parametrium cutting forceps the cutting blade is set in the illustrated, ineffective position which is determined by the engagement of the branch 4 in the catching recess 17. Then the forceps is opened by means of the grips 6 and 7 and if necessary by the disengagement of the locking indentations 8, so much that it can be pushed over the tissue to be seized e.g. the parametrium. When the forceps is open, the cutting blade is in the position indicated by the dot-and dash line in FIG. 4 which means that its cutting edge 10 is covered and ineffective. This renders impossible the premature opening of the cutting blade thus avoiding injury of the tissue and makes also impossible an inadvertent closing which could wound the tissue to be clamped and cut before the clasp has taken place. For this purpose, the catching force of the branch 4 in the catching recess 17 is choosen relatively high. After the clamping jaws 1 and 2 have been put over the section of the tissue to be clamped, the forceps is closed by means of the grips 6 and 7 and the tissue is clamped with the necessary force whereupon the forceps remains in the clamping position when the locking indentations 8 are engaged. The indentation of the clamping jaws prevent any slip of the forceps on the tissue or, inversely, of the tissue in the forceps. When closing the clamping jaws, the upper clamping jaw 1 brings the cutting blade 11 from the shoulder region 18 in the position illustrated in continuous line in FIG. 4 so that this cutting blade can work out the cutting motion by being swung upward. For this purpose the ring grip 13 is pressed downward until the catching force of the catching device is overcome. Due to the fact that this catching force is choosen of relatively high value, a sudden swing of the cutting blade takes place when the catch is disengaged which produces a sudden clear cut of the clamped tissue. For the sake of completeness it is mentioned that after the clamping procedure is completed the tissue which is at the opposite side of the clamping jaws as seen from the cutting blade is sewed before the above mentioned cutting operation by actuation of the cutting blade takes place. Because this additional working step takes place when the forceps is closed, that is when the cutting blade is outside of the region of the shoulder 18, it is particularly important to allow the cutting blade to be actuated only by overcoming of an important catching force, in order to prevent an inadvertent actuation of the cutting blade during the sewing procedure which would produce a premature injury of the tissue.

After the above described actuation of the cutting blade and the separation of the tissue have been completed, the cutting blade is set back in its catching position and the forceps is opened and the cutting blade reaches again its protecting, ineffective position below the shoulder 18. The forceps can then be put over a further section of the tissue to be clamped and separated and closed again and the described procedure may be repeated. In this manner it is possible to work properly and safely section by section whereby the position of the separating cut relatively to the clamped tissue's section is always exactly determined longitudinally and transversely.

Various executions are possible. The catching device for the cutting blade and its engagement beneath the shoulder 18 of the protecting ramp 19 is really a double security against inadvertent premature movements of the cutting blade. It would be possible as the case may arise to eliminate the shoulder 18 when only the cutting edge 10 of the cutting blade in the catching position of the latter lies at a side flank of the bed of the lower clamping jaw, such that this cutting edge is nowhere free. It would also be possible to provide both clamping jaws with clamping plates of hard metal. FIG. 2 shows a typical curvature of the clamping jaws and of the cutting blade which is appropriate for parametrium operations. In this case, the cutting blade lies at the inside with respect of the curvature. For other types of operations other straight clamping jaws or with another curvature and cutting blades of a corresponding form could be advantageous.

We claim:

1. Parametrium shearing forceps having clamping jaws, a locking device for stopping the clamping jaws in a clamping position, and a cutting blade, each of said clamping jaws having a single continuous clamping surface extending over substantially the full width of the clamping jaw, said cutting blade being provided on the side of the clamping jaws outside said clamping surfaces, said cutting blade having a cutting edge, an ineffective open position of said cutting blade for which its cutting edge is adjacent to the side of one clamping jaw and covered and protected by this one clamping jaw, a counter cutting edge at one side of the other of said clamping jaws, said cutting blade being displaceable from its ineffective position to a cutting position for shearing clamped tissue of a section of the length of the clamping jaws at the side of said clamping jaws, by cooperation of said cutting edges.

2. Forceps according to claim 1, wherein said one clamping jaw has a protective ramp, said cutting edge of the cutting blade being adjacent to said projecting ramp when the cutting blade is in its ineffective position.

3. Forceps according to claim 1, wherein said cutting blade is held in its ineffective open position by a catching recess exerting a catching effect onto a branch interconnected with the cutting blade.

4. Forceps according to claim 3, wherein a catching force is chosen of such a value that after releasing said branch from the catching recess, said clamped tissue is sheared suddenly.

5. Forceps according to claim 2, wherein upon closing of the clamping jaws said other clamping jaw pushes the cutting blade outwardly away from the protecting ramp, thereby allowing free motion of the cutting blade at the side of said other clamping jaw toward said one clamping jaw.

6. Forceps according to claim 1, wherein said clamping jaws are curved and wherein the cutting blade lies at the inside with respect to the curvature.

7. Forceps according to claim 1, comprising stop means for limiting the stroke of said cutting blade between the ineffective position adjacent to said one clamping jaw and its shearing end position.

8. Forceps according to claim 2, wherein said one clamping jaw has an asymmetrical profile at its free end, said profile having at one side an extension forming said ramp, the distance of such extension and ramp from the clamping surface of said one clamping jaw increasing toward the free end of said one clamping jaw.

* * * * *